(12) United States Patent
Mourier et al.

(10) Patent No.: US 8,518,909 B2
(45) Date of Patent: Aug. 27, 2013

(54) SULFATED HEPTASACCHARIDE AND ITS USE AS AN ANTITHROMBOTIC AGENT

(75) Inventors: Pierre Mourier, Paris (FR); Christian Viskov, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/288,577

(22) Filed: Nov. 3, 2011

(65) Prior Publication Data

US 2012/0108543 A1 May 3, 2012

Related U.S. Application Data

(63) Continuation of application No. PCT/IB2010/051932, filed on May 4, 2010.

(30) Foreign Application Priority Data

May 5, 2009 (EP) ..................................... 09290323

(51) Int. Cl.
*A61K 31/727* (2006.01)
*A61P 7/02* (2006.01)
*C08B 37/10* (2006.01)

(52) U.S. Cl.
USPC .............................................. 514/56; 536/21

(58) Field of Classification Search
USPC ............................................. 514/56; 536/21
See application file for complete search history.

(56) References Cited

U.S. PATENT DOCUMENTS

| | | | | |
|---|---|---|---|---|
| 4,401,662 A | * | 8/1983 | Lormeau et al. | 514/56 |
| 4,801,583 A | * | 1/1989 | Petitou et al. | 514/54 |
| 6,617,316 B1 | * | 9/2003 | Mourier et al. | 514/56 |
| 6,969,705 B2 | * | 11/2005 | Pecquet et al. | 514/56 |

FOREIGN PATENT DOCUMENTS

WO WO2010/128447 A1 11/2010

OTHER PUBLICATIONS

Guerrini et al, J. Biol. Chem., 2008, 283(39), 26662-75.*
Petitou, et al., 1976-1983, a Critical Period in the History of Heparin: The Discovery of the Antithrombin Binding Site, Biochimie, vol. 85, (2003), pp. 83-89.
Guerrini, et al., Antithrombin-Binding Octasaccharides and Role of Extensions of the Active Pentasaccharide Sequence in the Specificity and Strength of Interaction Evidence for Very High Affinity Induced by an Unusual Glucuonic Acid Residue, The Journal of Biological Chemistry, vol. 283, No. 39, pp. 26662-26675, (2008).
Hook, et al., Anticoagulant activity of heparin: Separation of high-activity and low-activity heparin species by affinity chromatography on immobilized antithrombin, FEBS Letters, vol. 66, Issue 1, Jul. 1, 1976, pp. 90-93.
Linhardt, 2003 Claude S. Hudson Award Address in Carbohydrate Chemistry. Heparin: Structure and Activity, Journal of Medicinal Chemistry, vol. 46, No. 13, (2003), pp. 2551-2564.
van Boeckel, et al., "The Unique Antithrombin III Binding Domain of Heparin: A Lead to New Synthetic Antithrombotics" Angewandte Chemie, International Edition in English; vol. 32, No. 12, Dec. 1993, pp. 1671-1818.

* cited by examiner

*Primary Examiner* — Shaojia Anna Jiang
*Assistant Examiner* — Ganapathy Krishnan
(74) *Attorney, Agent, or Firm* — Scully, Scott, Murphy & Presser, P.C.

(57) ABSTRACT

The instant invention relates to the heptasaccharide of formula (I):

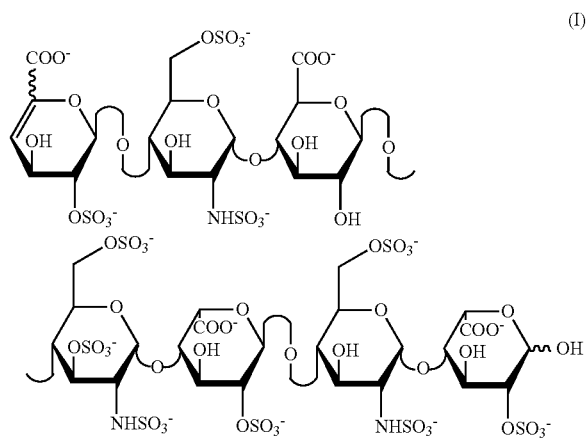

in its acid form or in the form of any one of its pharmaceutically acceptable salts, and to its process of preparation. The oligosaccharide of formula (I) is useful as an antithrombotic agent.

10 Claims, No Drawings

SULFATED HEPTASACCHARIDE AND ITS USE AS AN ANTITHROMBOTIC AGENT

The instant invention relates to a novel oligosaccharide, more specifically a sulfated heptasaccharide, and to its use as an antithrombotic agent.

Clotting is a defense mechanism preventing excessive loss of blood and ingestion of microbes. Yet, inadvertent formation and dislocation of clots may be harmful; antithrombotic drugs prevent the formation and growth of clots.

The Applicant has devised a novel approach for the identification of new antithrombotic compounds. Starting from oligosaccharides mixtures of LMWHs, specific analytical and separation methods have permitted to isolate an oligosaccharide endowed with advantageous antithrombotic properties, useful in anticoagulant therapy.

The oligosaccharide according to the instant invention responds to the formula (I), wherein the wavy lines denote bonds situated either below or above the plane of the pyranose rings:

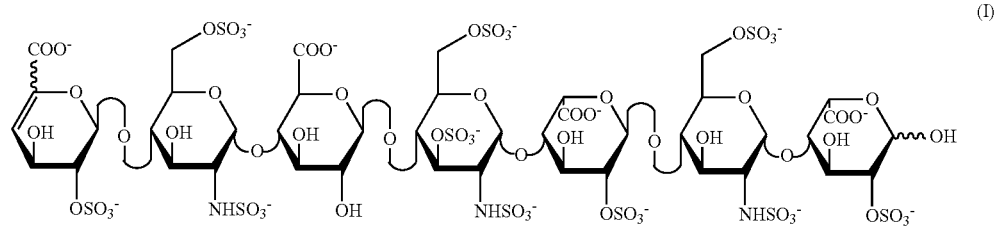

(I)

Heparin and Low Molecular Weight Heparins (LMWHs) are the current standard therapy in the management of thromboembolic diseases. Their anticoagulant activity is exerted through inhibition of coagulation factors, mainly activated factor X (FXa) and thrombin (factor IIa). This inhibitory action is mediated by the specific interaction of heparin species with antithrombin (AT), a serine protease inhibitor of the serpin family.

These drugs derive from animal sources: unfractionated heparin (UFH) is isolated from tissues such as lungs or intestinal mucosa, from porcine or bovine origins. LMWHs, such as tinzaparin, ardeparin, dalteparin, enoxaparin, nadroparin or reviparin, are obtained by enzymatic or chemical depolymerization of heparin.

Heparin and LMWHs are complex mixtures of molecules: they contain numerous sulfated polysaccharides, each of them being a polymer composed of a linear chain of monosaccharide residues. Therefore, the different polysaccharides present in heparin and in LMWHs vary in their lengths as well as in their chemical structures. The varying degree of sulfation and the presence of different 1→4 linked uronic acid and glucosamine disaccharide units give rise to a complex overall structure (J. Med. Chem., 2003, 46, 2551-2554).

Another class of antithrombotic drugs consists in synthetic oligosaccharides. Indeed, in the early 1980s it was determined that a unique pentasaccharide domain in some heparin chains is the minimal sequence required for binding and activating antithrombin III (Biochimie, 2003, 85, 83-89). Fondaparinux sodium is a synthetic analogue of this pentasaccharide, obtained through more than 60 steps of chemical synthesis. It is a selective inhibitor of factor Xa, commercialized for the prevention of thrombosis after orthopedic and abdominal surgery, for the prevention and treatment of deep vein thrombosis and pulmonary embolism, as well as for the treatment of coronary diseases.

Structure-based design has subsequently led to analogues with longer duration of action, such as idraparinux, displaying either selective factor Xa or dual Xa and IIa inhibition properties. The search for improved pharmacodynamic profiles lead to the synthesis of longer oligosaccharides, such as the clinical candidate SR123781 (hexadecasaccharidic compound), aiming at providing heparin mimetics that are more potent than heparin as regards antithrombin activity, but devoid of its side effects.

The oligosaccharide of formula (I) is a heptasaccharide. The invention encompasses the heptasaccharide of formula (I) in its acid form or in the form of any one of its pharmaceutically acceptable salts. In the acid form, the carboxylate (—COO$^-$) and sulfate (—SO$_3^-$) functional groups are respectively in the —COOH and —SO$_3$H forms.

The term "pharmaceutically acceptable salt" of the oligosaccharide of formula (I) is understood to mean an oligosaccharide in which one or more of the —COO$^-$ and/or —SO$_3^-$ functional groups are bonded ionically to a pharmaceutically acceptable cation. The preferred salts according to the invention are those for which the cation is chosen from the cations of alkali metals and more preferably still those for which the cation is sodium (Na$^+$).

In accordance with the present invention, the compound of formula (I) can be obtained from a LMWH product by using orthogonal (combined) separation methods selected from Gel Permeation Chromatography (GPC), AT affinity chromatography and anion exchange chromatography. According to the invention, these separation methods may be used in any possible combination thereof.

Gel Permeation Chromatography can be performed on columns filled with ACA202 (Prolabo) circulated with NaClO$_4$. Selected fractions are recovered by precipitation, for example by methanolic precipitation.

AT affinity chromatography can be performed on columns filled with AT-Sepharose. The stationary phase is prepared by coupling human AT (1 g; Biomed) to CNBr-activated Sepharose 4B (Sigma). The methodology of Höök et al. (FEBS Letters, 1976, 66(1), 90-3) is used to prepare the AT column, which is eluted with a NaCl gradient. The low-affinity portion is eluted from the column with a 0.25 M NaCl solution. The high-affinity heptasaccharide fraction is eluted with a 3 M NaCl solution. Affine fraction is desalted on column filled with Sephadex G-10 circulated with water.

Anion exchange chromatography can be achieved using AS11 (Dionex) semi-preparative HPLC columns. Any other anion exchange method may be performed, using other columns than Dionex AS11.

A final step for desalting the oligosaccharide thus obtained is performed, after neutralization of the collected fractions, in order to recover the oligosaccharide of the invention with the desired salt form. Methods for desalting oligosaccharides are well known to one of skill in the Art; mention may be made for example of desalting on a Sephadex G-10 column.

The following protocols describe in detail an example for the preparation of the compound (I) according to the invention, in the form of a sodium salt. They are included herewith for purposes of illustration only and are not intended to be limiting of the invention.

In this example, the compound (I) is prepared from a starting LMWH product by performing the following steps: Gel Permeation Chromatography (GPC), then ATIII affinity chromatography, and then anion exchange chromatography.

About 120 g of enoxaparin (commercially available from sanofi-aventis) are injected in 1 run in gel permeation on columns filled with ACA202 (Prolabo) circulated with $NaClO_4$ 0.2 M at 17 ml/min. The heptasaccharide fraction is gathered and desalted by precipitation: the fraction at about 2 mg/ml (oligosaccharide concentration) is added with sodium acetate (solution at 5% w/w) and precipitated at ambient temperature by the addition of 2 volumes of methanol. About 2 g of heptasaccharide fraction is thus obtained.

The entire heptasaccharide fraction is injected in ATIII affinity chromatography in about 10 runs where about 200 mg are injected on 30 cm×5 cm columns using elution with NaCl gradient. The low-affinity portion is eluted from the column with a 0.25 M NaCl solution buffered at pH 7.4 with 1 mM Tris at 6 ml/min. The high-affinity heptasaccharide fraction is eluted with 3 M NaCl solution buffered at pH 7.4 with 1 mM Tris at 6 ml/min. The detection is in UV at 232 nm.

Heptasaccharides eluted in affine fractions (about 120 mg) are gathered, desalted on Sephadex G-10 (100 cm×7 cm) and used as starting material for the next purification.

The purification is achieved in two runs by Dionex AS11 HPLC semi preparative chromatography, circulated with a $NaClO_4$ concentration gradient, for example with the following conditions:

Mobile phase: Solvent A: $NaH_2PO_4$, 2.5 mM, brought to pH 2.9 by adding $H_3PO_4$.

Solvent B: $NaClO_4$ in 1 N $NaH_2PO_4$, 2.5 mM, brought to pH 3.0 by adding $H_3PO_4$.

The elution gradient may be the following: T=0 min: % B=1; T=60 min: % B=80 and flow rate set at 20 ml/min. Detection is achieved in UV at 232 nm.

Fractions are controlled on Dionex AS11 HPLC analytical columns (250×2.1 mm), neutralized and desalted on Sephadex G-10.

Structural characterization of the heptasaccharide obtained, by NMR on a BRUCKER apparatus (600 MHz):

NMR $^1H$ in $D_2O$ (δ in ppm): between 3.10 and 3.3.30 (4H, m), between 3.50 and 4.50 (27H, m), 4.80 (2H, m), 4.96 (1H, s), 5.10 (1H, s broad), 5.16 (1H, s), 5.38 (2H, s), 5.42 (1H, s), 5.92 (1H, d, 4 Hz).

The oligosaccharide of the invention underwent pharmacological studies which demonstrated its antithrombotic properties and its value as therapeutically active substance.

Anti-FXa Activity in Plasma:

The ability of the sodium salt of the oligosaccharide (I) to accelerate AT-mediated FXa inhibition was analyzed in nearly physiological conditions. The anti-FXa activity measurement was performed using the competitive chromogenic assay STA®-Rotachrom® Heparin (Diagnostica Stago Inc.) automated on a STA®-R analyzer (Diagnostica Stago Inc.) according to the manufacturer's recommendation. Bovine FXa (Diagnostica Stago Inc.) was used. Fondaparinux was the reference material, obtained from commercial source marketed by GlaxoSmithKline. It was spiked at increasing concentrations (0.0218-0.0460-0.0872-0.1740-0.3490-0.4650 μmol/L) in normal pool human plasma (Hyphen).

Dose response linearity was demonstrated. The oligosaccharide of the invention and fondaparinux were tested at 6 concentrations ranging from 0.0218 to 0.4650 μM. The concentration of AT in plasma milieu was 2.25 μM. The measured absolute anti-Xa activity of the purified oligosaccharide was expressed in IU/ml, according to European Pharmacopeia 6.0 (01/2008:0828). The relative anti-FXa activity was calculated from the ratio of the absolute activity versus that of fondaparinux.

In this test, the oligosaccharide of the invention displays an absolute anti-FXa activity of 1.35 IU/ml. Its relative anti-Xa activity compared to fondaparinux is 1.65 fold.

The oligosaccharide of formula (I) according to the invention therefore displays high antithrombotic properties. It can be useful for the preparation of drugs, specifically of antithrombotic drugs. Therefore, another object of the invention is a medicament, which comprises an oligosaccharide of formula (I) or an addition salt thereof with a pharmaceutically acceptable salt.

Such a medicament is useful in therapeutics, in particular in the treatment and prevention of thromboses, including venous thromboses (for example in the post-operative phase of surgical patients, in cancer patients or in medical patients with restricted mobility) and acute arterial thrombotic events, in particular in the case of myocardial infarction.

Another object of the invention is also a pharmaceutical composition, which comprises, as active principle, an oligosaccharide of formula (I) according to the present invention. Such a pharmaceutical composition comprises an effective dose of an oligosaccharide of formula (I) according to the invention, or an addition salt thereof with a pharmaceutically acceptable salt, and at least one pharmaceutically acceptable excipient. Said excipients are chosen according to the pharmaceutical form and the administration route desired, among usual excipients known to one of skill in the art.

The pharmaceutical compositions according to the invention may comprise, in addition to the oligosaccharide of formula (I), at least one other active principle selected from antithrombotic oligosaccharides, whether synthetic compounds (obtained by chemical, stepwise synthesis starting from appropriate mono- or oligosaccharidic building blocks) or compounds isolated from heparin or LMWHs sources.

In the pharmaceutical compositions according to the invention for the oral, sublingual, sub-cutaneous, intramuscular, intra-venous, topical, local, intratracheal, intranasal, transdermal or rectal administration, the active principle of formula (I) above, or its salt, can be administered as a unitary dosage form, in blend with usual pharmaceutical excipients, to animals and human beings for the prevention or for the treatment of the pathologies mentioned above.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compound of the invention may be used as creams, gels, ointments or lotions.

The present invention, according to another of its aspects, also relates to a method for the treatment and prevention of the above pathologies, which comprises the administration to a patient of an effective dose of the oligosaccharide of formula (I) according to the invention, or a salt with a pharmaceutically acceptable salt thereof.

What is claimed is:

1. An isolated and purified oligosaccharide of formula (I):

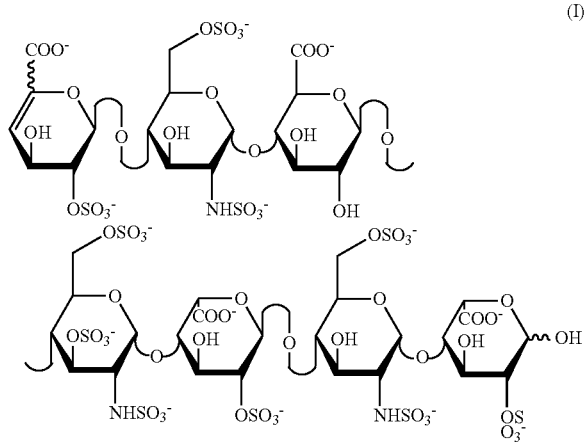

wherein the wavy lines denote bonds situated either below or above the plane of the pyranose rings,
in its acid form or in the form of any one of its pharmaceutically acceptable salts.

2. The oligosaccharide according to claim 1, in the form of its sodium salt.

3. A process for the preparation of an oligosaccharide according to claim 1, which comprises steps for separating said oligosaccharide from a starting Low Molecular Weight Heparin (LMWH) product by performing Gel Permeation Chromatography (GPC), AT affinity chromatography and anion exchange chromatography, in any possible combination of those methods.

4. The process according to claim 3, which comprises the following steps:
   a) Gel Permeation Chromatography (GPC), then
   b) AT affinity chromatography, and then
   c) anion exchange chromatography.

5. The process according to claim 3, wherein the anion exchange chromatography is performed on Dionex AS11 HPLC columns.

6. The process according to claim 3, wherein the starting LMWH product is enoxaparin.

7. A pharmaceutical composition, comprising an oligosaccharide of formula (I) according to claim 1, or a pharmaceutically acceptable addition salt thereof, and at least one pharmaceutically acceptable excipient.

8. The pharmaceutical composition according to claim 7, further comprising at least one other active principle selected from antithrombotic oligosaccharides.

9. A method for the treatment of thromboses in a patient comprising administering to the patient an oligosaccharide of formula (I) according to claim 1, or a pharmaceutically acceptable addition salt thereof.

10. The method according to claim 9, wherein the thromboses are venous thromboses or acute thrombotic events.

\* \* \* \* \*